Figure 1:
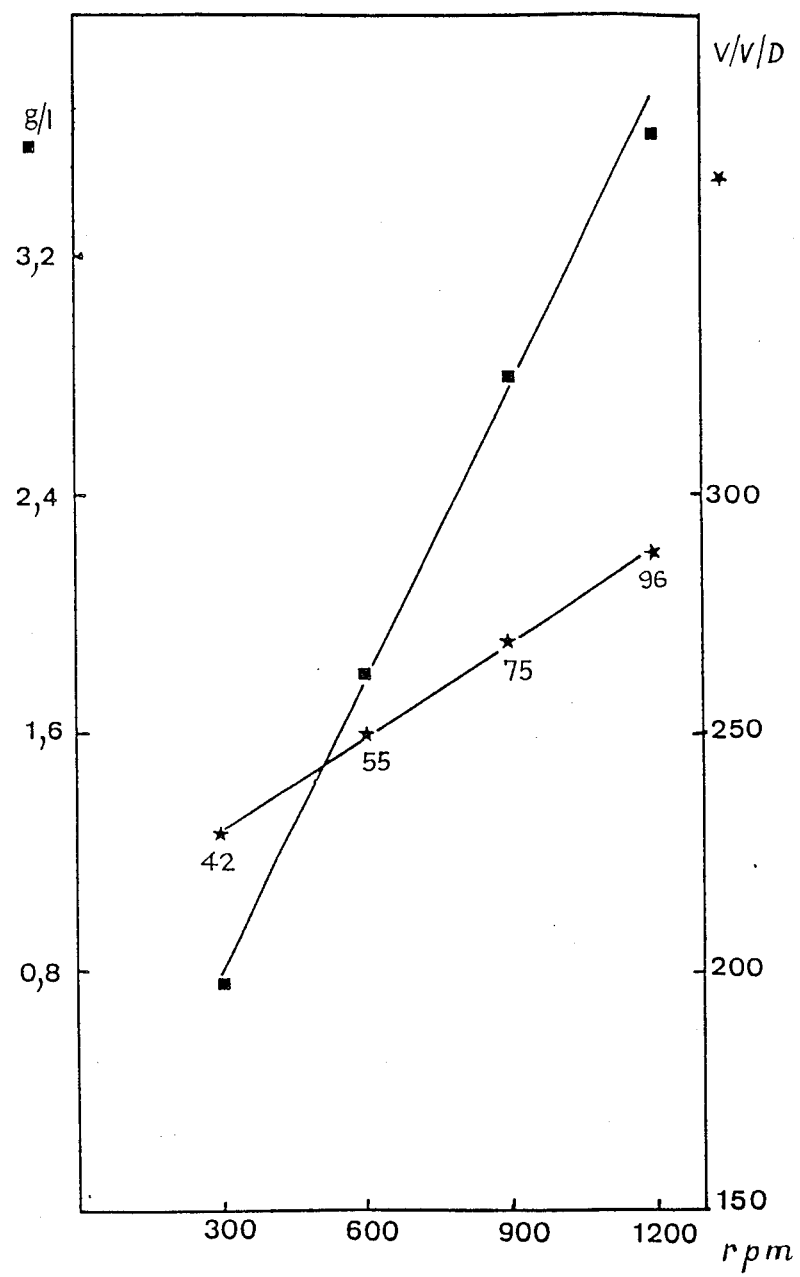

United States Patent [19]

Belaich et al.

[11] Patent Number: 4,883,753
[45] Date of Patent: Nov. 28, 1989

[54] **HIGH-YIELD METHANE PRODUCTION PROCESS BY CULTURE OF *METHANOBACTERIUM THERMOAUTOTROPHICUM* OR ANY OTHER METHANOGENIC BACTERIUM HAVING THE SAME PHYSIOLOGICAL GROWTH PROPERTIES**

[75] Inventors: Jean-Pierre Belaich, Marseilles; Marie-Laure Fardeau, Pennes Mirabeau; Jean-Paul Peillex; André Pavia, both of Montpellier, all of France

[73] Assignee: Gaz De France, France

[21] Appl. No.: 74,284

[22] Filed: Jul. 16, 1987

[30] Foreign Application Priority Data

Jul. 17, 1986 [FR] France ................................ 86 10431

[51] Int. Cl.$^4$ .............................................. C12P 5/02
[52] U.S. Cl. ..................................... 435/167; 435/170; 435/822
[58] Field of Search .................. 435/167, 822, 170

[56] References Cited

U.S. PATENT DOCUMENTS 4,540,666  9/1985  Nukina et al. ...................... 435/167

FOREIGN PATENT DOCUMENTS 2236489  10/1987  Japan .................................... 435/167
721823   1/1955   United Kingdom .
2107735  8/1982   United Kingdom .

OTHER PUBLICATIONS

Chemical Abstracts No. 178,192m, vol. 84, 1976.
Commercially Prepared Abstract SU-992-569-A.
Kluyver et al., "On the Fermentation of Carbon Monoxide by Pure Cultures of Methane Bacteria", *Arch. Biochem.*, vol. 14, Nos. 1 and 2 (Jul. 1947).
Daniels et al., "Considerations for the Use and Large Scale Growth of Methanogenic Bacteria", *Biotechnology and Bioengineering Symp.* No. 14, (1984), pp. 199–213.

*Primary Examiner*—Herbert J. Lilling
*Attorney, Agent, or Firm*—Ostrolenk, Faber, Gerb & Soffen

[57] ABSTRACT

This invention relates to a high-yield methane production process, comprising cultivating on a culture medium containing a source of nitrogen and assimilable salts, the methanogenic bacterium *Methanobacterium thermoautotrophicum* or any other methanogenic bacterium having the same physiological growth properties, with a forced supply of gaseous $H_2/CO_2$ mixture.

4 Claims, 3 Drawing Sheets

HIGH-YIELD METHANE PRODUCTION PROCESS BY CULTURE OF *METHANOBACTERIUM THERMOAUTOTROPHICUM* OR ANY OTHER METHANOGENIC BACTERIUM HAVING THE SAME PHYSIOLOGICAL GROWTH PROPERTIES

The present invention relates to a high-yield methane production process by culture of *Methanobacterium thermoautotrophicum* or other methanogenic bacterium having the same physiological growth properties, under particular conditions.

It is well known that methane may be produced by so-called methanogenic bacteria. Among such bacteria figure the hydrogenophilic methanogenic bacteria, which are capable of producing methane from a gaseous $CO_2$—$H_2$ mixture. Certain of these bacteria are also thermophilic, in particular *Methanococcus thermolitotrophicus* and *Methanobacterium thermoautotrophicum*.

The physiological properties of the bacterium *Methanococcus thermolithotrophicus* and more precisely the growth energetics of this organism have been described by Fardeau and Belaich in Arch. Microbiol. (1986) 114: 381–385.

The bacterium *Methanobacterium thermoautotrophicum* has been studied by several research teams and is described in particular by:

Schönheit et al. in Arch. Microbiol. 127, 59–64 (1980);

Seely et al. in Biochem. Biophys. Rest. Comm. 116: 1125–1128 (1983);

Brandis et al. in Zbl. Bakt. Hyg. Abt. Grig. (2, 311–317 (1981)), and

Daniel et al in Bioeng. 14: 199–213 (1984).

Most of these researchers have studies this bacterium in discontinuous culture (or "batch" culture). The conditions of culture recommended by these authors do not make it possible to obtain high productivity and percentage of methane in the gaseous effluent of the fermenter.

Furthermore, work carried out by Applicants have demonstrated that it was possible to attain with the thermophilic methanogenic bacteria very considerable specific methane production activities (372 $m^3$ of methane per day and per kg, dry weight, of bacteria), but that it was necessary to find a biotechnological or biological solution making it possible to increase the percentage of methane in the effluent and the productivity of the reactor by increase of the active biomass. In fact, despite the considerable specific activity of the thermophilic methanogenic bacteria, the productivity of the fermenters was very low, of the order of 30 V/V/D. The same applies to the maximum biomasses obtained in non-renewed medium, which did not exceed, for I Methanococcus thermolitotrophicus (MTL), the value of 0.8 g dry weight/liter. The results of productivity were qualitatively identical for the second bacterium used: *Methanobacterium thermoautotrophicum* (MTA), although the biomass obtained in the fermenter was higher (5 g/l).

Up to the present time, it was therefore unthinkable to envisage production of methane on an industrial scale by culture of one or the other of the bacteria mentioned hereinabove.

It has now been found that methane may be obtained with both a high productivity and high methane yield in the effluent produced, by continuous culture of *Methanobacterium thermoautotrophicum* or any other methanogenic bacterium having the same physiological growth properties with forced supply of gas, i.e. with a high gas transfer velocity.

The present invention therefore relates to a process for the production of methane with high yield which involves cultivating the above bacteria continuously on an adequate culture medium and with forced supply of $H_2/CO_2$ gas. In this way, by employing a gas transfer velocity of at least 60 liters of $CO_2/H_2$ mixture per liter and per hour, at least 96% of the gas entering the fermenter is transformed into methane.

The gas transfer velocity is determined from the productivity of methane multiplied by five.

For the purposes of the invention, this velocity must be at least 50 liters per liter and per hour.

Culture of *Methanobacterium thermoautotrophicum* or of any other methanogenic bacterium having the same physiological growth properties is effected in a fermenter on a culture medium essentially containing a source of nitrogen and a source of assimilable salts.

An example of composition of the appropriate culture medium for the purpose of the invention is given hereinbelow:

| | |
|---|---|
| $KH_2PO_4$ | 50 mM |
| NaCl | 40 mM |
| $NH_4Cl$ | 50 mM |
| $Na_2CO_3$ | 19 mM |
| Titriplex I | 0.5 mM |
| $MgCl_2$ | 0.2 mM |
| $FeCl_2$ | 50 μM |
| $COCl_2$ | 1 μM |
| $Na_2MoO_4$ | 1 μM |
| $Ni(NO_3)_2$, 6 $H_2O$ | 5 μM |
| Cysteine hydrochloride | 2.86 mM |
| $Na_2S$, 9 $H_2O$ | 2.1 mM |

Such a medium must be prepared under anaerobic conditions and sterilized for example for about 20 minutes at about 110° C.

The process of the invention is carried out at the temperature at which the bacterium multiplies, for example, for *Methanobacterium thermoautotrophicum*, at a temperature of about 65° C.

The fermenter is supplied with substrate constituted by hydrogen and carbon dioxide in an appropriate ratio, for example in an $H_2/CO_2$ ratio of 80/20%.

Supply of the fermenter with gaseous substrate is advantageously effected by a diffuse made of sintered glass or any other porous material of low porosity giving a very weak gas bubble size distribution with respect to the liquid volume and which is placed below the stirring turbine necessary for the dispersion of these bubbles and for the turbulence of the medium.

Measurement of the transfer capacities of the turbine-diffuser assembly may be effected by following oxidation of a solution of sulfite by the oxygen in the air. The coefficient of gas transfer measured by this method, called $K_L$, attained a value of 3000 $h^{-1}$ at 65° C. for 60 liter/liter/hour of air at the inlet and for a stirring speed of 600 rpm, whilst its maximum value for the fermenters equipped with a conventional diffusion ring does not exceed 1500 $h^{-1}$ under the same conditions.

It is now possible, thanks to the process of the invention, to obtain a high yield of $CH_4$, i.e. a productivity of at least 250 V/V/D of methane with a percentage of at least 85% in the effluent.

The invention will now be described in detail by the following non-limiting Example:

EXAMPLE

An Interscience "Labo 2000" fermenter was used, on which were added two bent tubes made of sintered glass (porosity 0) between the turbine and the magnetic coupler for driving the turbine.

The fermenter was used at its maximum heating power without the cooling system.

Stirring being adjustable from 300 to 1200 rpm, the best results were obtained from 900 rpm.

The working volume was 1 liter.

The culture medium defined hereinabove was used. This liquid culture medium, stored in a 20 l flask under anaerobic conditions (with continuous $H_2/CO_2$ stream), was conveyed to the fermenter with the aid of a peristaltic pump ("Masterflex") in thick silicon pipes ("Victoria"). The gas supply flowrate was controlled by an electronic regulation adapted to the system. The substrate was constituted by a gaseous $H_2/CO_2$ mixture in an 80/20±0.4% ratio ("Prodair")

The liquid level in the fermenter was adjusted by a tube flush with the surface and common to the outlet of the gases and of the medium, a slight excess pressure of the gas causing evacuation of the excess liquid until flush with the tube. The effluent was collected in a sterile storage flask under anaerobic conditions.

The incoming and outgoing gas flows were measured with the aid of flowmeters.

The pH and redox potential were measured regularly but not regulated.

The outlet gases were cooled in order to condense the water vapour and analyzed by gaseous phase chromatography.

Figure 2:
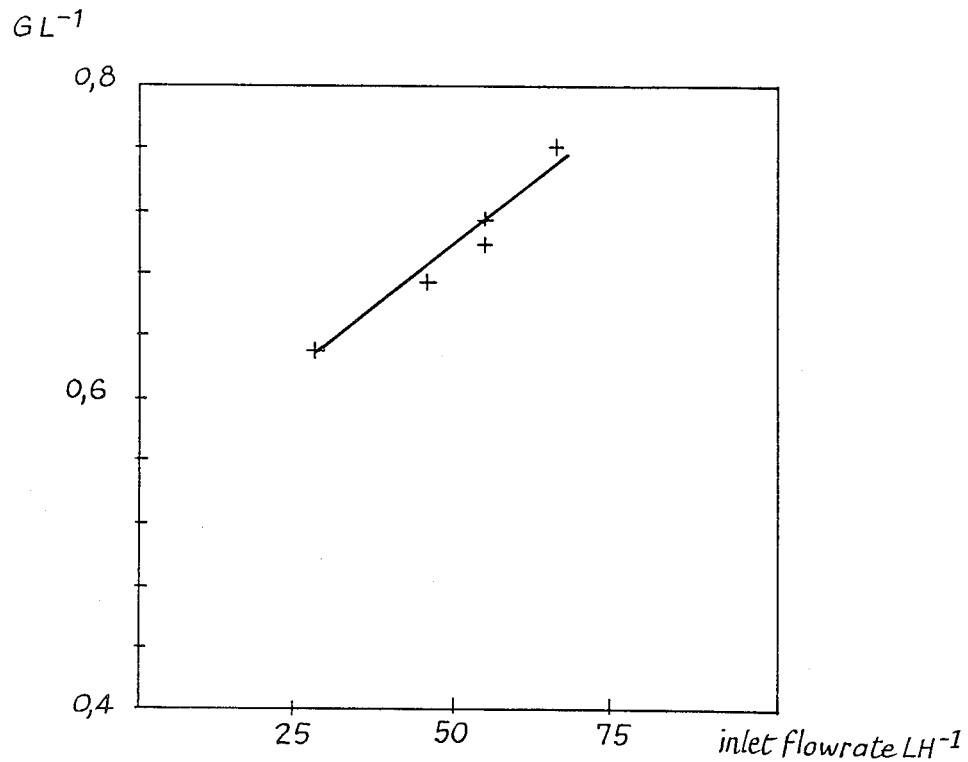
Figure 3:
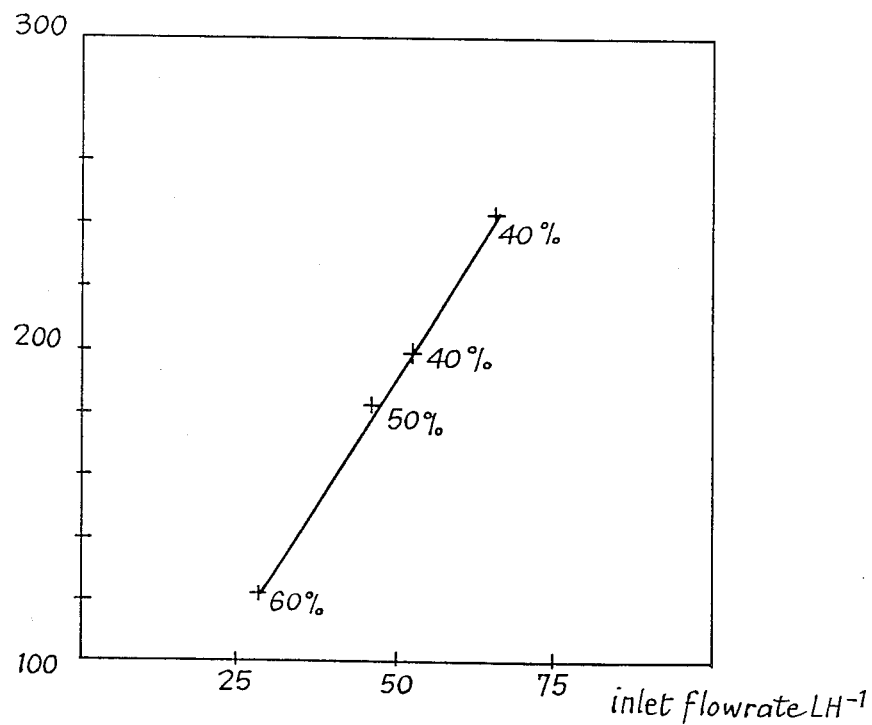

The results obtained with *Methanobacterium thermoautotrophicum* are shown in accompanying FIGS. 1 to 3, which represent, respectively:

FIG. 1: the productivity of $CH_4$ (right-hand y-axis: V/V/D) and of biomass (left-hand y-axis: g/l) of *Methanobacterium thermoautotrophicum* as a function of the speed of stirring with constant rate of dilution and flowrate of $CO_2/H_2$ at the inlet; the percentages of $CH_4$ in the effluent are indicated on the curve.

FIG. 2: the productivity of biomass (g/l) of *Methanobacterium thermoautotrophicum* as a function of the inlet flowrate of the gaseous mixture with constant rate of dilution and speed of stirring.

FIG. 3: the productivity of $CH_4$ (V/V/D) of *Methanobacterium thermoautotrophicum* as a function of the inlet flowrate of the gaseous mixture with constant rate of dilution and speed of stirring; the percentages of $CH_4$ in the effluent are indicated on the curve.

FIG. 1 clearly shows that the biomass, in the stationary state, of the fermenter is proportional to the speed of rotation of the turbine. The culture of MTA passes from a cellular concentration of 0.8 g/l to 3.6 g/l; at the same time, the productivity of the reactor passes from 228 to 288 V/V/D and the percentage of methane in the gaseous effluent from 42 to 96%. FIGS. 2 and 3 show that, for a constant rate of dilution and speed of stirring, the biomass and the productivity of the reactor are proportional to the flowrate of the supply gas of the culture ($H_2/CO_2$ mixture. The best pair (percentage of $CH_4$ in the effluent, productivity of the reactor) obtained was 96% of $CH_4$ and 288 V/V/D for a speed of rotation of the turbine of 1200 rpm, the inlet flowrate being 60.5 l/hr., the outlet flowrate 12.5 l/hr., and the biomass 3.6 g/l dry weight.

These results are all the more surprizing and original as similar experiments carried out with *Methanococcus thermolitotrophicus* did not enable the same productivity of $CH_4$ to be attained. The maximum productivities obtained in this case are always less than 80 V/V/D with a percentage of methane in the effluent of about 50%.

All these tests show that the process of the invention results both from the selection of the particular methanogenic bacteria having specific physiological properties of growth and from specific culture conditions.

What is claimed is:

1. A process for producing methane with high yield comprising the step of cultivating on a culture medium containing a source of nitrogen and assimilable salts and thermophilic methanogenic bacterium having the same physiological growth properties as *Methanobacterium thermoautotrophicum* with a forced supply of gaseous $H_2/CO_2$ mixture having a gas transfer velocity of at least 50 liters of $H_2/CO_2$ mixture per liter and per hour.

2. The process of claim 1, wherein the bacterium is *Methanobacterium thermoautotrophicum*.

3. The process of claim 1, wherein the gas transfer velocity is at least 60 liters per liter.

4. The process of claim 3, wherein the medium is stirred at 300 to 1200 rpm per hour.

* * * * *